United States Patent [19]

Rzeszotarski et al.

[11] Patent Number: 5,036,107

[45] Date of Patent: Jul. 30, 1991

[54] 1,7-SUBSTITUTED HEPTYN-2-ONES AND USE

[75] Inventors: Waclaw J. Rzeszotarski, Millersville; Maria E. Guzewska; Daniel W. McPherson, both of Baltimore; Ciro J. Spagnuolo, Cockeysville; Kenneth J. Natalie, Jr., Baltimore, all of Md.

[73] Assignee: Marion Merrell Dow Inc., Kansas City, Mo.

[21] Appl. No.: 437,165

[22] Filed: Nov. 16, 1989

Related U.S. Application Data

[63] Continuation of Ser. No. 155,110, Feb. 11, 1988, abandoned, which is a continuation-in-part of Ser. No. 42,959, Apr. 27, 1987, abandoned, which is a continuation-in-part of Ser. No. 879,397, Jun. 27, 1986, abandoned.

[51] Int. Cl.$^5$ .................. A61K 31/135; C07C 225/18
[52] U.S. Cl. .................. 514/648; 514/653; 514/906; 514/929; 514/930; 514/935; 564/342; 564/345
[58] Field of Search ............... 564/315, 319, 320, 342, 564/345; 514/648, 929, 930, 935, 906, 653

[56] References Cited

U.S. PATENT DOCUMENTS

| | | | |
|---|---|---|---|
| 2,717,895 | 9/1955 | Sprague et al. | 564/319 X |
| 2,759,926 | 8/1956 | Reppe et al. | 564/319 X |
| 2,835,676 | 5/1958 | Sprague et al. | 564/319 X |
| 3,176,019 | 3/1965 | Campbell et al. | 560/58 X |

OTHER PUBLICATIONS

Burger, "Medicinal Chemistry", 3rd. Ed., Part I, p. 75 (1970).

The Merck Index, 10th Ed., p. 997, Section No. 6823 (1983).

*Primary Examiner*—Richard L. Raymond
*Attorney, Agent, or Firm*—Theresa M. Gillis

[57] ABSTRACT

1-Phenyl-7-substituted-hept-5-yn-2-ones substituted with a $C_1$ to $C_7$ alkyl, $C_3$ to $C_6$ cycloalkyl, aryl, heteroaryl or heterocycloalkyl group at the 1-position and an amino, a dialkylamino, a piperidyl, a pyrrolidyl or a hexahydroazepinyl group at the 7-position are disclosed which may have one or two substituents in addition to the phenyl group at the 1-position and also may have a p-fluoro substituent on the phenyl group. The preferred compounds are, 1-cyclohexyl-1-phenyl-1-hydroxy-7-dimethylaminohept-5-yn-2-one, 1-cyclobutyl-1-phenyl-1-hydroxy-7-dimethylaminohept-5-yn-2-one and 1-cyclo-1-phenyl-1-hydroxy-7-ethylaminohept-5-yn-2-one.

The compounds are highly specific $M_1$-AChR antagonists with relatively prolonged duration of activity. They are particularly useful in the treatment of neurogenic bladder disorders and may be administered orally or parenterally in conventional formulations containing optional conventional additives such as binders, surfactants, emulsifiers, flavorants, preservatives and the like.

11 Claims, No Drawings

1,7-SUBSTITUTED HEPTYN-2-ONES AND USE

This is a continuation of application Ser. No. 07/155,110, filed Feb. 11, 1988, now abandoned, which is a continuation-in-part of pending U.S. application Ser. No. 07/042,959 filed Apr. 27, 1987, now abandoned, which is a continuation-in-part of U.S. application Ser. No. 06/879,397 filed June 27, 1986, now abandoned.

BACKGROUND OF THE INVENTION

1. Field of Invention

This invention relates to novel 1-phenyl-7-substituted-aminohept-5-yn-2-ones optionally mono-or di-substituted at the 1-position, their pharmaceutically acceptable salts, their use in the treatment of neurogenic bladder disease and methods for their manufacture.

2. State of the Art

Neurogenic bladder disease is defined as a disorder involving loss of control of urinatior. The major symptoms can be urinary frequency, urinary retention or incontinence.

There are two types of lesions that come under the rubric of neurogenic bladder. The first, upper motoneuron lesion, leads to hypertonia and hyperreflexia of the bladder, a spastic condition, giving rise to symptoms of urinary frequency and incontinence. The second lesion, a lower motoneuron lesion, involves hypotonia and hyporeflexia of the bladder, and in more severe conditions complete distension and atonia of the bladder muscle. Thus, this is a flaccid condition. The major symptoms in this condition are urinary retention, since the voiding reflex has been lost, and incontinence, which occurs when the bladder "leaks", being full to overflowing.

The flaccid or hypotonic bladder is the easier condition to treat. The aim in treatment is to produce a contraction of the bladder, while avoiding contraction of the bladder neck or the urethra. Parasympathomimetic compounds (cholinergic agonists) are commonly employed to stimulate the excitatory muscarinic receptor on the bladder smooth muscle. The most widely used compound in this class is bethanechol, a muscarinic receptor agonist. This is given in combination with the alpha-adrenergic antagonist phenoxybenzamine to prevent sympathetic stimulation of the bladder neck muscle. Bethanechol is also sometimes given in combination with baclofen, a skeletal muscle receptor antagonist. In general, however, urologists and internists have been moving away from pharmacological treatment of the hypotonic bladder, and prefer to institute the physical maneuver of intermittent catheterization.

The majority of neurogenic bladder patients have the spastic or hypertonic condition, which is usually more difficult to treat. In this instance, the usual aim of the clinician is to attempt to convert the condition of hyperreflexia and hypertonia to hypotonia, thereby treating the primary problem of incontinence. When the condition has been converted to hypotonia it can be straightforwardly managed by intermittent catheterization. There is a significant population of patients who cannot be converted completely from the hypertonic to the hypotonic condition, and who still find that they have to urinate every hour. For these patients, longer term treatment with an anticholinergic drug (muscarinic receptor antagonist) is necessary. The current drug of choice is oxybutynin, which is considered to be better than older anticholinergic treatments such as methantheline and propantheline. Although relatively high doses of oxybutynin are in general use (5 mg q.i.d.), tachycardia is not a major side effect of this compound, unlike classical muscarinic receptor antagonists such as atropine. On the other hand, the most frequent side effect of oxybutynin treatment is dry mouth.

Recent advances in the muscarinic receptor field have suggested that oxybutynin is an antagonist with a fair degree of selectivity for the $M_1$-AChR type of receptor, thereby explaining both the lack of cardiac side effects (heart tissue has predominantly $M_2$-AChR) and the occurrence of the dry mouth side effect (salivary glands have predominantly an $M_1$-AChR population).

Although oxybutynin chloride is used in the treatment of neurogenic bladder disorder, it exhibits a relatively short duration of action and, as indicated above, causes dry mouth. The compounds of the present invention contain a methylene group in lieu of the non-carbonyl (i.e., esteratic) oxygen of oxybutynin chloride. These novel compounds exhibit advantages relative to oxybutynin chloride in terms of their efficacy and specificity of action against neurogenic bladder disorder. In particular, the compounds of the invention are longer acting antimuscarinic agents which have spasmolytic action.

SUMMARY OF THE INVENTION

The invention provides novel compounds of the formula:

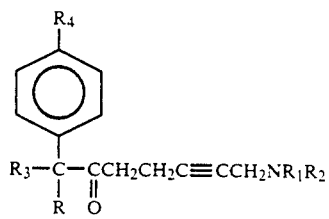

wherein:
R is an alkyl having one to seven carbon atoms, cycloalkyl having three to six carbon atoms, polycycloalkyl of seven to eleven carbon atoms, or substituted or unsubstituted aryl, heterocycloalkyl, or heteroaryl;

$R_1$ and $R_2$ independently are hydrogen, alkyl having one to three carbon atoms, phenylalkyl, said alkyl having one to three carbons or $R_1R_2$ is —$(CH_2)n$— where n is an integer of 4 to 6;

$R_3$ is hydrogen, hydroxy or fluorine; and $R_4$ is hydrogen or fluorine and their pharmaceutically acceptable salts. The compounds are selective muscarinic acetylcholine receptor (M-AChR) antagonists having particular activity in the treatment of neurogenic bladder disorder.

DETAILED DESCRIPTION OF THE INVENTION

The present invention encompasses compounds of the formula:

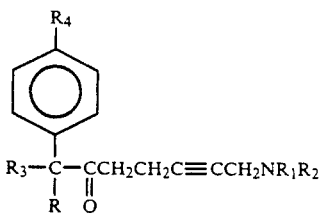

and their pharmaceutically acceptable salts. In the foregoing formula, R is a $C_1$ to $C_7$ alkyl chain; $C_3$ to $C_6$ cycloalkyl such as cyclohexyl and cyclopentyl; aryl including phenyl; polycycloalkyl having seven to eleven carbon atoms; substituted aryl, wherein the substituents include halogen, preferably fluoro, hydroxy, nitro, methoxy, methyl, trifluoromethyl, acetyl or amino; heterocycloalkyl, such as five and six membered cyclic compounds containing one or two nitrogens preferably bonded to the above noted formula by a methylene group; heteroaryl; polycycloaryl, such as naphthyl and tetrahydronaphthyl; and substituted heteroaryl or heterocyclo wherein the substituents may be selected from among those permitted as aryl substituents. Among the heterocyclic substituents suitable in the above formula are pyridyl, including both 3-pyridyl and 4-pyridyl, and five and six membered fully saturated rings having one nitrogen or having two nitrogens opposite to one another with such ring being bonded to the formula recited above through a methylene group bonded to one of the nitrogens or to a saturated carbon opposite to the single nitrogen of a six-membered ring. Where the heterocyclic compound is substituted, the substituent is a methyl or an acetyl —$C(O)CH_3$ group. In particular, preferred saturated heterocyclic R substituents include:

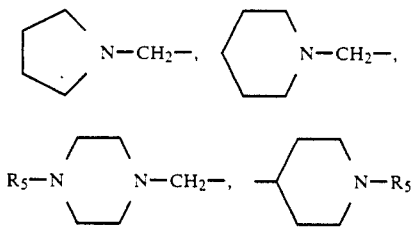

$R_5$ is selected from a one to three carbon alkyl, acetyl, and phenylethyl. R is preferably aryl, cycloalkyl or polycycloalkyl and most preferably phenyl, cycloalkyl of 4 or 6 carbons or adamantyl. When R is phenyl it is preferably para-substituted, most preferably by a fluoro substituent. $R_1$ and $R_2$ are each independently hydrogen, a one to three carbon alkyl, particularly methyl or ethyl, phenylalkyl, such as phenylethyl, or $R_1$ and $R_2$ together with the nitrogen form a heterocyclo group having four to six carbons. $R_3$ is hydrogen, hydroxy or fluorine. $R_4$ is hydrogen or fluorine.

Salts of the compounds of the invention include the acid salts such as the hydrochloride, sulfate, phosphate, nitrate, methanesulfonate and tartrate salts. Other pharmaceutically acceptable salts are also included in the invention, as are the various possible hydrates of each of the compounds. As will be understood by those skilled in the art, compounds of this invention may be present as d or l optical isomers as well as racemic mixtures thereof. Further some of the compounds in which R is a substituted cycloalkyl or a polycycloalkyl may be present as enantiomers which may be resolved into optical isomers. Resolution of optical isomers may be accomplished by fractional crystallization of their diostereomeric salts with optically active acids such as, for example, tartaric, camphor-10-sulfonic, O, O-dibenzoyltartaric, O, O-di(p-toluoyl) tartaric, menthyloxyacetic, camphoric, or 2-pyrrolidone-5-carboxylic acids or N-acetyltryptophane from appropriate solvents. They may also be prepared by stereoselective synthesis or by chromatographic techniques using chiral substrates or derivatives. Unless otherwise specified in the claims, it is intended to include all isomers, whether separated or mixtures thereof.

The preferred compounds of the invention are those in which R is phenyl, cyclohexyl, cyclopropyl, cyclobutyl, cyclopentyl, or polycycloalkyl and $R_1$ and $R_2$ are independently hydrogen, methyl or ethyl. The most preferred compounds are 1-cyclohexyl-1-phenyl-1-hydroxy-7-dimethylaminohept-5-yn-2-one, 1-cyclohexyl-1-phenyl-1-hydroxy-7-methylaminohept-5-yn-2-one and 1-cyclohexyl-1-phenyl-1-hydroxy-7-ethylaminohept-5-yn-2-one, 1-cyclobutyl-1-hydroxy-1-phenyl-7-dimethylaminohept-5-yn-2-one and 1-bicyclo[2.2.1] hept-2-yl-1-hydroxy-1-phenyl-7-dimethylaminohept-5-yn-2-one. Compounds within the invention include:

2-Hydroxy-2-phenyl-8-(N,N-diethylamino)oct-6-yn-3-one

1-Cyclohexyl-1-hydroxy-1-phenyl-7-diisopropylaminohept-5-yn-2-one

1-Cyclohexyl-1-hydroxy-1-phenyl-7-ethylaminohept-5-yn-2-one

1-Cyclohexyl-1-hydroxy-1-phenyl-7-(N-methyl-N-ethylamino)hept-5-yn-2-one

1-Cyclohexyl-1-hydroxy-1-phenyl-7-isopropylaminohept-5-yn-2-one

1-Cyclohexyl-1-hydroxy-1-phenyl-7-(N-methyl-N-isopropylamino)hept-5-yn-2-one

1-Cyclohexyl-1-phenyl-7-diethylaminohept-5-yn-2-one

1-Cyclohexyl-1-hydroxy-1-phenyl-7-t-butylaminohept-5-yn-2-one

1-Cyclohexyl-1-hydroxy-1-phenyl-7-(N-ethyl-N-isopropylamino)hept-5-yn-2-one

1-Cyclohexyl-1-hydroxy-1-phenyl-7-dimethylaminohept-5-yn-2-one

1-Cyclohexyl-1-hydroxy-1-phenyl-7-(N-methyl-N-phenethylamino)-hept-5-yn-2-one

1-Cyclohexyl-1-hydroxy-1-phenyl-7-pyrrolidinylhept-5-yn-2-one 1-(6-N,N-Diethylaminohex-4-yn-2-one)-1-hydroxyindan 1-Cyclohexyl-1-hydroxy-1-phenyl-7-methylaminohept-5-yn-2-one 1-Cyclohexyl-1-fluoro-1-phenyl-7-diethylaminohept-5-yn-2-one 1-Cyclohexyl-1-hydroxy-1-phenyl-7-(N,N-diethyl-N-methylammonio)hept-5-yn-2-one 1-Cyclohexyl-1-hydroxy-1-phenyl-7-(N-methyl-N-benzylamino)hept-5-yn-2-one 1-Cyclopentyl-1-hydroxy-1-phenyl-7-(N-methyl-N-ethylamino)hept-5-yn-2-one 1-Cyclopropyl-1-hydroxy-1-phenyl-7-diethylaminohept-5-yn-2-one 1-Cyclohexyl-1-hydroxy-1-phenyl-7-aminohept-5-yn-2-one 1-Cyclohexyl-1-hydroxy-1-phenyl-7-di-n-butylaminohept-5-yn-2-one 1-Cyclopentyl-1-hydroxy-1-phenyl-7-dimethylaminohept-5-yn-2-one 5-(6-N,N-Diethylamino-1-oxohex-4-ynyl)-5-hydroxy-6,7,8,9-tetrahydrobenzocycloheptene 1-Cyclopropyl-1-hydroxy-1-phenyl-7-(N-methyl-N-ethylamino)hept-5-yn-2-one 1-Cyclohexyl-1-hydroxy-1-phenyl-7-(dipropylamino)-hept-5-yn-2-one 1,1-Diphenyl-1-hydroxy-7-ethylaminohept-5-yn-2-one 1,1-Diphenyl-1-hydroxy-7-(N-ethyl-N-methylamino)-hept-5-yn-2-one 1,1-Diphenyl-1-hydroxy-7-dimethylaminohept-5-yn-2-one 1,1-Cyclopropyl-1-hydroxy-1-phenyl-7-ethylaminohept-5-yn-2-one 1-Cyclopropyl-1-hydroxy-1-phenyl-7-dimethylaminohept-5-yn-2-one 1-Cyclohexyl-1-hydroxy-3-methyl-1-phenyl-7-dimethylamino-hept-5-yn-2-one 1-(1-Adamantyl)-1-hydroxy-1-phenyl-7-dimethylaminohept-5-yn-2-one 1-Cyclohexyl-1-hydroxy-1-(4-fluorophenyl)-7-dimethylaminohept-5-yn-2-one 1-Cyclohexyl-1-hydroxy-1-(4-fluorophenyl)-7-ethylaminohept-5-yn-2-one (S)-1-Cyclohexyl-1-hydroxy-1-phenyl-7-dimethylaminohept-5-yn-2-one 1-Cyclohexyl-1-hydroxy-1-phenyl-7-[N-(2-hydroxyethyl)-N-methylamino]hept-5-yn-2-one 1-Bicyclo [2.2.1] hept-2-yl-1-hydroxy-1-phenyl-7-dimethylaminohept-5-yn-2-one 1-Bicyclo [2.2.1] hept-2-yl-1-hydroxy-1-phenyl-7-ethylaminohept-5-yn-2-one (R)-1-Cyclohexyl-1-hydroxy-1-phenyl-7-dimethylaminohept-5-yn-2-one 1-Cyclobutyl-1-hydroxy-1-phenyl-7-dimethylaminohept-5-yn-2-one 1-Cyclobutyl-1-hydroxy-1-phenyl-7-ethylamino-hept-5-yn-2-one 1-Cyclobutyl-1-hydroxy-1-phenyl-7-(N-ethyl-N-methylamino) hept-5-yn-2-one 3-Hydroxy-2-methyl-3-phenyl-9-dimethylaminonon-7-yn-4-one 1-(1-Methylcyclopropyl)-1-hydroxy-1-phenyl-7-dimethylaminohept-5-yn-2-one 4-Hydroxy-2-methyl-4-phenyl-10-dimethylamino-dec-8-yn-5-one Particularly preferred compounds include 1-cyclohexyl-1-hydroxy-1-phenyl-7-dimethylaminohept-5-yn-2-one and 1-cyclobutyl-1-hydroxy-1-phenyl-7-dimethylaminohept-5-yn-2-one.

The compounds of the invention have a greater affinity toward $M_1$-AChR than $M_2$-AChR and are selective in their pharmacological action. The high selectivity of the compounds of the invention, in particular 1-phenyl or 1-cyclohexyl or 1-cyclopentyl-1-phenyl-1-hydroxy-7-diethylaminohept-5-yn-2-one, has been demonstrated in receptor binding studies, functional assays and isolated organs by their ability to provide a selective antagonism of the $M_1$-AChR.

The compounds may be administered in a variety of pharmaceutical preparations well known to those skilled in the pharmaceutical arts. For parenteral administration, the compounds may be prepared in aqueous injection solutions which may contain antioxidants, buffers, bacteriostats, and other additives commonly employed in such solutions. Extemporaneous injection solutions may be prepared from sterile pills, granules or tablets which may contain diluents, dispersing and surface active agents, binders, and lubricants, as well as the compound of the invention.

In the case of oral administration, fine powders or granules of the compound of the invention may be formulated with diluents and dispersing and surface active agents, and may be prepared in water, a syrup, capsules cachets, a non-aqueous suspension or an emulsion. In dry forms optional binders and lubricants may be present. The compositions may also include flavorants, preservatives, suspending, thickening and emulsifying agents and other pharmaceutically acceptable additives. Granules or tablets for oral administration may be coated.

The compounds are useful in the treatment of patients suffering from neurogenic bladder disorders. The compounds are administered in pharmaceutically effective amounts; that is the amount necessary to produce an anticholinergic effect. Dosing can be determined by correlation of the $M_1$-AChR activity of the compounds of the invention with the known $M_1$-AChR activity of oxybutynin chloride. Typically, the compounds of the invention can be expected to have a longer duration of action thereby permitting a reduced number of doses without loss of activity. Moreover, the acceptable upper dose limits for compounds of the invention can be higher than for oxybutynin chloride insofar as the compounds of the invention show more selectivity, that is, fewer side effects, than oxybutynin chloride.

The compounds of the invention can be prepared by a variety of synthetic routes. One of these sequences involves Mannich condensation of pent-4-yn-1-ol with formaldehyde and the appropriate amine followed by sequential oxidation of the alcohol to an aldehyde, conversion of the aldehyde to a dithiane, condensation of the dithiane with a requisite aryl ketone and lastly dithiane deprotection to the 1,7-substituted hept-5-yn-2-one. Another method involves addition of lithium acetylide to the aryl ketone, oxidation of the resulting acetylide to a methyl ketone which is sequentially propargylated to give an acetylenic derivative which is subjected to appropriate Mannich condensation. Alternatively, the methyl ketone can be alkylated with 1,4-dibromo-2-butyne to give a bromo derivative that can be alkylated to provide the product. In an alternative route the aryl ketone can be condensed with 1-(diethoxyphosphinyl) ethoxytrimethylsilane to give a methyl ketone that is propargylated and aminomethylated to give the product. Another sequence begins with an appropriate disubstituted glycolic acid which is converted to the methyl ketone that is transformed to product via the aforementioned propargylation, Mannich condensation sequence. According to another method a 1-dialkoxyphosphinyl-1-trialkyl silyloxyethane having one to four carbons in one each of the alkyl and alkoxy groups is condensed with a ketone of the formula $R_6$-C(O)-R in which R has the meanings set forth in the general formula above and $R_6$ is a phenyl or p-fluorophenyl group; the resulting 1,1-disubstituted-1-trialkylsilyloxy-2-propanone is propargylated followed by Mannich reaction of the product with formaldehyde and an amine having the formula $HNR_1R_2$ in which $R_1$, and $R_2$ have the meanings set forth in the general formula above; and the silyl protecting group is thereafter removed. Yet another route for synthesizing the compounds involves ethynylation of a ketone to give a 3,3-disubstituted-3-hydroxypropyne which is oxidized to the corresponding 2-propanone; alkylating the product with 1,4-dibromo-2-butyne to produce a 1,1-disubstituted-1-hydroxy-7-bromohept-5-yn-2-one which is aminated to give a compound of the invention. Obviously, many other routes to the requisite 1,7-substituted hept-5-yn-2-ones can be devised. The following examples are illustrative of compounds of the invention and their manufacture. In the following examples melting points and boiling points are given in degrees Centigrade, NMR signals are given in p.p.m. using $Me_4Si$ as an internal standard and IR data are given in $cm^{-1}$.

EXAMPLES

EXAMPLE I

6-Diethylaminohex-4-yn-1-ol

A mixture of paraformaldehyde (7.14 g, 238 mmol), diethylamine (27.6 ml, 260 mmol) and cupric acetate monohydrate (1 g) in dioxane (40 ml) was heated in an oil bath of 60° C. for 1 hour. When the solid material disappeared, pent-4-yn-1-ol (20 g, 238 mmol) was added and the heating at 95° C. was continued until the greenish suspension had been completely replaced by the thin brown precipitate (approximately 3 hours). After cooling to 20° C., the reaction mixture was poured into 10% aqueous KOH (40 ml). The precipitate was filtered off and washed with ether (100 ml). The organic phase was washed with water (5 times 50 ml), dried ($K_2CO_3$) and evaporated to dryness to give crude product. The isolated product was distilled to yield 29.78 g (74%) of 6-diethylaminohex-4-yn-1-ol: bp 92°–94° C. (0.1 mm Hg), IR (neat) 3309 $cm^{-1}$; $^1H$ NMR ($CDCl_3$) δ4.1(S, 1H), 3.6(t, 2H), 3.3(m, 2H), 2.7–2.0(m, 6H), 2.0–1.4(m, 2H), 1.0(t, 6H).

6-Diethylaminohex-4-ynal

A solution of dimethyl sulfoxide (25.1 ml, 353 mmol) in $CH_2Cl_2$ (75 ml) was added to the stirred solution of oxalyl chloride (14.75 ml, 169 mmol) in $CH_2Cl_2$ (370 ml) at −60° C. The reaction mixture was stirred for 1 hour and a solution of 6-diethylaminohex-4-yn-1-ol prepared as above (25 g, 147.5 mmol) in $CH_2Cl_2$ (150 ml) was added dropwise; stirring was continued for an additional hour. TEA (103.25 ml, 740 mmol) was added and the reaction mixture was stirred for 90 minutes and then allowed to warm to room temperature. Water (200 ml) was then added and the aqueous layer was reextracted with chloroform (3 times 100 ml). The organic layers were combined, washed with brine and dried ($MgSO_4$). Evaporation of solvent yielded crude product, which was filtered through silica gel and distilled to give 19.26 g (78%) of an aldehyde: bp 68°–71° C. (0.125 mm Hg), IR (neat) 1727.9 $cm^{-1}$; $^1H$ NMR ($CDCl_3$) δ9.7(s, 1H), 3.3(m, 2H), 2.7–2.2(m, 8H), 1.0(t, 6H).

2-(5-Diethylaminopent-3-yn)-1,3-dithiane

A solution of the above prepared 6-diethylaminohex-4-ynal (10 g, 59.7 mmol) and 1,3-propanedithiol (6 ml, 59.7 mmol) in $CH_2Cl_2$ (150 ml) was stirred for 1 hour and then treated with $BF_3.Et_2O$ (8 ml). After 5 hours, the reaction mixture was successively washed three times each with water, 10% aqueous KOH solution and water. The organic layer was dried ($K_2CO_3$), filtered, and freed of solvent. Chromatography of the residue on silica gel with hexane/ethyl acetate/triethylamine (95:5:3) followed by distillation afforded 4.3 g (28%) of the dithiane: bp 140° C. (0.2 mm Hg); IR (neat) 907.7 $cm^{-1}$; $^1H$ NMR ($CDCl_3$) δ4.1(t, 1H), 3.4(m, 2H), 2.8–1.8(m, 14H), 1.1(t, 6H). Anal. Calcd. for $C_{13}H_{23}NS_2$: C, 60.65; H, 9.00; N, 5.44; S, 24.91. Found: C, 60.70; H, 9.04; N, 5.42; S, 24.82.

1-Cyclohexyl-1-phenyl-1-hydroxy-7-diethylaminohept-5-yn-2-one bis (1,3-propylene) dithioketal To the foregoing dithiane (5 g, 19.42 mmol) in 100 ml of dry THF cooled to −70° C. was added dropwise 11.4 ml (25 mmol) of 2.2M n-BuLi. After 45 minutes at this temperature, the reaction mixture was warmed to −20° C. and TMEDA (3.76 ml, 25 mmol) was added. After 1 hour at this temperature, the light yellow solution was cooled to −70° C. and a solution of cyclohexylphenylketone (3.64 g, 19.4 mmol) in 50 ml of dry THF was introduced. The reaction mixture was stirred for additional 3 hours, then quenched with water, and extracted with ether. The extract was dried ($K_2CO_3$) and freed of solvent. The crude isolated product was chromatographed on silica gel with hexane/ethyl acetate/triethylamine (95:5:3) to yield 6.40 g (74%) of product: IR (neat): 3486.7 $cm^{-1}$; $^1H$ NMR ($CCl_4$) δ7.8–7.1(m, 5H), 3.2(m, 2H), 2.9–1.3(m, 26H), 1.0(t, 6H). Hemioxalate: mp 172°–3° C. (EtOH); IR (nujol) 1625.1 $cm^{-1}$. Anal. Calcd. for $C_{27}H_{40}NO_3S_2$: C, 66.08; H, 8.22; N, 2.85; S, 13.06. Found: C, 66.18; H, 8.36; N, 2.82; S, 12.95.

1-Cyclohexyl-1-phenyl-1-hydroxy-7-diethylaminohept-5-yn-2-one

Thallium (III) nitrate trihydrate (3.13 g, 6.9 mmol) in methanol (15 ml) was rapidly added to the above dithioketal (3 g, 6.73 mmol) dissolved in MeOH (120 ml) and THF (30 ml). A white precipitate formed immediately and after 5 minutes, $CH_2Cl_2$ (100 ml) was added and the precipitate was filtered. The solvent was removed in vacuum and the residue dissolved in chloroform, washed with water and dried ($MgSO_4$). Evaporation of solvent gave crude 1-cyclohexyl-1-phenyl-1-hydroxy-7-diethylaminohept-5-yn-2-one, which was chromatographed on C-18 silica gel with acetonitrile/MeOH (98:2) to give 340 mg (14.22%) of the desired product: IR (neat) 1709.9 $cm^{-1}$; $^1H$ NMR ($CDCl_3$) δ7.6–7.2(m, 5H), 3.4(m, 2H), 2.9–2.3(m, 9H), 2.0–1.0(m, 17H). Oxalate: mp 112°–115° C. (EtOH); IR ($CHCl_3$) 1779.8, 1704.8 and 1655.9 $cm^{-1}$. Anal. Calcd. for $C_{25}H_{35}NO_6$: C, 67.39; H, 7.92; N, 3.14. Found: C, 67.43; H, 7.95; N, 3.10.

EXAMPLE II

1-Cyclopentyl-1-phenyl-1-hydroxy-7bis (1,3-propylene) dithioketal

To the dithiane prepared in Example I (5 g, 19.42 mmol) in 100 ml of dry THF cooled to −70° C. was added dropwise 11.4 ml (25 mmol) of 2.2M n-BuLi. After 45 minutes at this temperature, the reaction mixture was warmed to −20° C. and TMEDA (3.76 ml, 25 mmol) was added. After 1 hour at this temperature, the light yellow solution was cooled to −70° C. and a solution of cyclopentyl phenyl ketone (3.3 ml, 19.42 mmol) in 50 ml of dry THF was introduced. The reaction mixture was stirred for additional 3 hours, then quenched with water, and extracted with ether. The extract was dried ($K_2CO_3$) and the solvent removed in vacuum. The crude isolated product was chromatographed on silica gel with hexane/ethyl acetate/triethylamine (95:5:3) to yield 6.37 g (76%) of product: IR (neat): 3517.5 $cm^{-1}$. $^1H$ NMR ($CCl_4$) δ7.7–7.0(m, 5H), 3.2(m, 2H), 2.9–1.1(m, 24H), 1.0(m, 6H). Oxalate: mp 139°–140° C. (EtOH); IR (Nujol) 1740.8 and 1653.3 cm$^{-1}$; Anal. Calcd. for $C_{27}H_{39}NO_5S_2$: C, 62.16; H, 7.53; N, 2.68; S, 12.29. Found: C, 62.00; H, 7.59; N, 2.63; S, 12.21.

1-Cyclopentyl-1-phenyl-1-hydroxy-7-diethylaminohept-5-yn-2-one

Thallium (III) nitrate trihydrate (3.13 g, 6.9 mmol) in MeOH (15 ml) was rapidly added to the foregoing product (2.9 g, 6.73 mmol) dissolved in MeOH (120 ml) and THF (30 ml). A white precipitate formed immediately and after 5 minutes, $CH_2Cl_2$ (100 ml) was added and the precipitate was filtered. The solvents were removed from the filtrate in vacuum and the residue dissolved in chloroform, washed with water and dried ($MgSO_4$). Evaporation of solvent gave crude product, which was chromatographed on C-18 silica gel with acetonitrile/MeOH (98:2) to give 0.77 g (33.62%) of the desired product: IR (neat): 1709.9 cm$^{-1}$; $^1$H NMR (CDCl$_3$) δ7.6–7.1(m, 5H), 3.3(m, 2H), 2.8–2.1(m, 10H), 1.8–1.3(m, 8H); 1.1(m, 6H). Oxalate: mp 128°–129° C. (EtOH); IR (CHCl$_3$): 1776.8, 1704.8 and 1653.3 cm$^{-1}$. Anal. Calcd. for $C_{24}H_{33}NO_5$: C, 66.80; H, 7.70; N, 3.24. Found: C, 66.81; H, 7.74; N, 3.20.

EXAMPLE III

1,1-Diphenyl-1-hydroxy-7-diethylaminohept-5-yn-2-one bis (1,3-propylene) dithioketal To the dithiane prepared in Example I (5 g, 19.42 mmol) in 100 ml of dry THF cooled to −70° C. was added dropwise 11.4 ml (25 mmol) of 2.2M n-BuLi. After 45 minutes at this temperature, the reaction mixture was warmed to −20° C. and TMEDA (3.76 ml, 25 mmol) was added. After 1 hour at this temperature, the light yellow solution was cooled to −70° C. and a solution of benzophenone (3.53 g, 19.4 mmol) in 50 ml of dry THF was introduced. The reaction mixture was stirred for additional 3 hours, then quenched with water, and extracted with ether. The extract was dried ($K_2CO_3$) and freed of solvent. The crude isolated product was chromatographed on silica gel with hexane/ethyl acetate/triethylamine=95:5:3 to yield 6.16 g (72.13%) of product: IR (CHCl$_3$) 3437.8 cm$^{-1}$; $^1$H NMR (CDCl$_3$) δ7.9–7.0(m, 10H), 4.2(s, 1H), 3.2(m, 2H), 2.6–1.4(m, 14H), 0.9(t, 6H).

1,1-Diphenyl-1-hydroxy-7-diethylaminohept-5-yn-2-one

Thallium (III) nitrate trihydrate (3.13 g, 6.9 mmol) in $CH_3OH$ (15 ml) was rapidly added to the dithiane (Example III) (2.95 g, 6.73 mmol) dissolved in $CH_3OH$ (120 ml) and THF (30 ml). A white precipitate formed immediately and after 5 minutes, $CH_2Cl_2$ (100 ml) was added and the precipitate was filtered. The solvent was removed from the filtrate in vacuum and the residue dissolved in chloroform, washed with water and dried ($MgSO_4$). Evaporation of solvents afforded crude product, which was chromatographed on C-18 silica gel with acetonitrile/MeOH (98:2) to give 0.35 g (15%) of the desired product. IR (CHCl$_3$) 1710.0 cm$^{-1}$; $^1$H NMR (CDCl$_3$) δ7.35(s, 10H), 3.3(m, 2H), 2.8(t, 2H), 2.5(m, 6H), 1.0(t, 6H).

EXAMPLE IV

6-Diisopropylaminohex-4-yn-1-ol

A mixture of paraformaldehyde (7.14 g, 238 mmol), diisopropylamine (19.1 ml, 262 mmol) and cupric acetate monohydrate (1 g) in dioxane (40 ml) was heated in an oil bath of 60° C. for 1 hour. When the solid material disapeared, pent-4-yn-1-ol (20.02 g, 238 mmol) was added and the heating at 95° C. was continued until the greenish suspension had been completely replaced by a thin brown precipitate (approximately 3 hours). After cooling to 20° C., the reaction mixture was poured into 10% aqueous KOH (40 ml). The precipitate was filtered off and washed with ether (100 ml). The organic phase was washed with water (5 times 50 ml), dried ($K_2CO_3$) and evaporated to dryness to give the crude product. The isolated product was distilled to yield 16.88 g (36%) of 6-diisopropylaminohex-4-yn-1-ol: bp 116°–9° C. (0.05 mm Hg); $^1$H NMR (CDCl$_3$) δ1.08(d, 12H), 1.40–1.98(m, 2H), 2.02–2.60(m, 2H), 2.83–3.44(m, 4H), 3.46–3.83(t, 2H), 4.09(s, 1H).

6-Diisopropylaminohex-4-ynal

A solution of dimethyl sulfoxide (25.1 ml, 353 mmol) in $CH_2Cl_2$ (75 ml) was added to a stirred solution of oxalyl chloride (14.75 ml, 169 mmol) in $CH_2Cl_2$ (370 ml) at −60° C. The reaction mixture was stirred for 1 hour and a propylamino-solution of 6-diisopropylaminohex-4-yn-1-ol (29.07 g, 147.5 mmol) in $CH_2Cl_2$ (150 ml) was added and the reaction mixture was stirred for 90 minutes and then allowed to warm to room temperature. Water (200 ml) was then added and the aqueous layer was reextracted with chloroform (3 times 100 ml). The organic layers were combined, washed with brine and dried ($MgSO_4$). Evaporation of the solvent yielded crude product, which was distilled to give 12.96 g of the aldehyde: bp 90-5 (0.25 mm Hg); $^1$H NMR (CDCl$_3$) δ1.05(d, 12H), 2.00–2.67(m, 4H), 2.83–3.50(m, 4H), 9.67(s, 1H).

2-(5-Diisopropylaminopent-3-yne)-1,3-dithiane

A solution of 6-diisopropylaminohex-4-ynal (11.66 g, 59.7 mmol) and 1,3-propanedithiol (6 ml, 59.7 mmol) in $CH_2Cl_2$ (150 ml) was stirred for 1 hour and then treated with $BF_3.Et_2O$ (8 ml). After 5 hours the reaction was successively washed three times each with water, 10% aqueous KOH solution and water. The organic layer was dried ($K_2CO_3$), filtered, and freed of solvent. Chromatography of the residue on silica gel with hexane/ethyl acetate/triethylamine (95:5:3) followed by distillation afforded 2.28 g (13%) of the dithiane: bp 150°–54° C. (0.1 mm Hg); $^1$H NMR (CDCl$_3$) δ0.91–1.50(d+m, 14H), 1.68–2.67(m, 6H), 2.73–3.67(m, 6H), 4.18(t, 1H).

1-Cyclohexyl-1-phenyl-1-hydroxy-7-diisopropylaminohept-5-yne-2-one bis (1,3-propylene) dithioketal To the dithiane (5.54 g, 19.42 mmol) in 100 ml of dry THF cooled to −70° C. 10.0 ml (25 mmol) of 2.5M n-BuLi was added dropwise. After 45 minutes at this temperature, the reaction mixture was warmed to −20° C. and TMEDA (3.76 ml, 25 mmol) was added. After 1 hour at this temperature, the light yellow solution was cooled to −70° C. and a solution of cyclohexyl phenyl ketone (4.70 g, 25 mmol) in 50 ml of dry THF was introduced. The reaction mixture was stirred for an additional 3 hours, then quenched with water, and extracted with ether. The extract was dried ($K_2CO_3$) and freed of solvent. The crude isolated product was chromatographed on silica gel with hexane/ethyl acetate/triethylamine (95:5:3) to yield 1.64 g (30%) of product.

1-Cyclohexyl-1-phenyl-1-hydroxy-7-diisopropylaminohept-5-yne-2-one

Thallium (III) nitrate trihydrate (3.13 g, 6.9 mmol) in methanol (15 ml) was rapidly added to the foregoing dithioketal, (3.19 g, 6.73 mmol) dissolved in MeOH (120 ml) and THF (30 ml). A white precipitate formed immediately and after 5 minutes, $CH_2Cl_2$ was added and the precipitate was filtered. The solvent was removed in vacuum and the residue dissolved in chloroform, washed with water and dried ($MgSO_4$). Evaporation of solvent gave crude product, which was chromatographed on C-18 silica gel with acetonitrile/MeOH (98:2) to give the desired product.

EXAMPLE V

3-Cyclohexyl-3-hydroxy-3-phenylprop-1-yne

Lithium acetylide (47.84 g, 0.52 mol) was added to 70 ml of dry tetrahydrofuran (THF). The solution was cooled to 0° C. and a solution of cyclohexyl phenyl ketone in 100 ml of dry THF was added over a period of 15 minutes with stirring. The solution was allowed to warm to room temperature and stirred for 16 hours. The solution was then cooled to 0° C. and 50 ml of a 5N HCl solution was added with. The solution was then warmed to room temperature and 200 ml of water was added. The solution was transferred to a separatory funnel and washed with ether. The ether washes were combined and dried over sodium sulfate. Upon removal of the ether under vacuum and vacuum distillation of the crude product a pale yellow oil was isolated (60.33 g, 82.9%). Bp 111°–14° C. (0.8 mm). $^1H$ NMR ($CDCl_3$) δ7.7–7.2(m, 5H), 2.6(s, 1H), 2.3(s, 1H), 2.1–0.9(m, 11H). IR (neat) 3433, 3304, 2111, 1448, 1016 $cm^{-1}$.

1-Acetoxy-1-cyclohexyl-1-phenylpropan-2-one

3-Cyclohexyl-3-hydroxy-3-phenylprop-1-yne (21.57 g, 0.10 mol) was added to 100 ml of glacial acetic acid. While the solution was stirred vigorously mercuric acetate (35.20 g, 0.11 mol) was added. The solution was stirred at room temperature for 72 hours and then thioacetamide (8.3 g, 0.11 mol) was added. The solution was stirred an additional 3 hours and 300 ml of ether was added. The reaction mixture was transferred to a separatory funnel and washed with water, saturated sodium bicarbonate solution, and again with water. The ether layer was dried over sodium sulfate and the ether removed under vacuum to afford the product as a white crystalline solid (18.36 g, 66.9%). Mp 81°–83° C. (from petroleum ether). $^1H$ NMR ($CDCl_3$) δ7.3(bs, 5H), 2.2(s, 3H), 1.9(s, 3H), 2.0–0.8(m, 11H).

1-Cyclohexyl-1-hydroxy-1-phenylpropan-2-one

To a solution of 1-acetoxy-1-cyclohexyl-1-phenylpropan-2-one (16.42 g, 0.06 mol) in 55 ml of a 90% aqueous methanol solution was added 3.2 g of potassium hydroxide. The solution was refluxed for 15 minutes, cooled, and 90 ml of a saturated sodium chloride was added. The reaction mixture was transferred to a separatory funnel and washed with ether. The ether washes were combined, dried over sodium sulfate, and evaporated to dryness under vacuum. The crude product was vacuum distilled to afford a clear oil (10.51 g, 75.4%). Bp 125°–28° C. (0.1 mm). $^1H$ NMR ($CDCl_3$) δ7.6–7.2(m, 5H), 4.5(s, 1H), 2.1(s, 3H), 2.5–0.9(m, 11H). IR (neat) 3456, 3057, 1705, 1448, 1358, 1209, 1124 $cm^{-1}$.

1-(Trimethylsilyloxy)-1-cyclohexyl-1-phenylpropan-2-one

1-Cyclohexyl-1-hydroxy-1-phenylpropan-2-one is added to dry acetonitrile and the solution is stirred. Bis(trimethylsilyl)acetamide is then added and the reaction mixture is heated at 30° C. for 1 hour. The solution is then cooled and evaporated to dryness under vacuum to afford the product as a white crystalline solid after recrystallization.

1-(Trimethylsilyloxy)-1-cyclohexyl-1-phenylhex-5-yn-2-one

Lithium diisopropylamide is dissolved in dry THF and the solution cooled to −78° C. A solution containing 1-(trimethylsilyloxy)-1-cyclohexyl-1-phenylpropan-2-one in dry THF is added dropwise to the stirring solution at −78° C. After the addition is complete the reaction mixture is stirred for 1 hour. Then a solution of propargyl bromide in dry THF is added dropwise to the solution at −78° C. The solution is then warmed to 0° C. and stirred for 5 hours. An ether-acetic acid solution (9:1) is slowly added and the resultant mixture warmed to room temperature. Ether is added and the solution transferred to a separatory funnel and washed with water. The ether layer is dried over sodium sulfate and evaporated to dryness to afford the product as a white crystalline solid after recrystallization.

1-Cyclohexyl-1-hydroxyl-1-phenylhex-5-yn-2-one 1-(Trimethylsilyloxy)-1-cyclohexyl-1-phenylhex-5-yn-2-one is dissolved in methanol containing 1% concentrated hydrochloric acid at 25° C. Water is added and the solution transferred to a separatory funnel. The solution is washed with ether and the ether layer dried over sodium sulfate. Upon evaporation of the ether under vacuum and vacuum distillation of the crude product a pale yellow oil is isolated.

1-Cyclohexyl-1-hydroxy-1-phenyl-7-diethylaminohept-5-yn-2-one

A mixture of paraformaldehyde, diethylamine, and cupric acetate monohydrate in dioxane is heated at 60° C. for 1 hour. 1-Cyclohexyl-1-hydroxy-1-phenylhex-5-yn-2-one is then added and the reaction mixture heated at 95° C. for 5 hours. The mixture is cooled and added to a 10% potassium hydroxide solution. The solution is washed with ether and the ether extracts are dried over sodium sulfate and evaporated to dryness under vacuum. The crude product is distilled to give a white crystalline solid as its oxalate salt.

Also prepared by the general method described in Example 6 utilizing phenyl cyclobutyl ketone, phenyl isopropyl ketone, phenyl methyl ketone and phenyl isobutyl ketone with the appropriate secondary amine were 1-cyclobutyl-1-hydroxy-1-phenyl-7-dimethylaminohept-5-yn-2-one, 1-cyclobutyl-1-hydroxy-1-phenyl-7-(N-ethyl-N-methylamino)hept-5-yn-2-one, 3-hydroxy-2-methyl-3-phenyl-9-dimethylaminonon-7-yn-4-one, 1-(1-methylcyclopropyl)-1-hydroxy-1-phenyl-7-dimethylaminohept-5-yn-2-one, and 4-hydroxy-2-methyl-4-phenyl-10-dimethylaminodec-8-yn-5-one.

EXAMPLE VI

1-Cyclohexyl-1-phenyl-1-trimethylsilyloxy-2-propanone

To a stirred solution of 35 ml (0.25 mole) of diisopropylamine in 800 ml of THF at −78° C. was added 100 ml of a 2.5M solution of n-BuLi in hexane. After the mixture was stirred at −78° C. for 1 hour, 52 g (0.205 mole) of 1-(diethoxyphosphinyl)-1-trimethylsilyloxyethane [prepared according to the procedure of G. H. Birum and G. A. Richardson, U.S. Pat. No. 3,113,139 (1963)] was added dropwise. The mixture was stirred for 1.5 hours at −78° C. and then 42.5 g (0.225 mole) of cyclohexyl phenyl ketone in 100 ml of THF was added dropwise at −78° C. The stirred solution was warmed to room temperature during 30 minutes and then it was poured into 2 L of water. Extraction of the mixture with ether, after washing with dilute hydrochloric acid, drying and concentrating gave 51 g (75%) of colorless liquid.

1-Cyclohexyl-1-phenyl-1-siloxy-hex-5-yn-2-one

To a stirred solution of 140 ml (0.65 moles) of hexamethyldisilazane in 1.6 L of dry THF cooled to −78° C. was added 280 ml of a 2.5M solution of n-BuLi in hexane. The mixture was stirred and warmed to −5° C. over a 0.5 hour period. The siloxy ketone (192 g, 10.632 moles) was added as a solution in 100 ml of THF and stirred at −5° C. for 1 hour. This was then added to a solution of 200 ml (1.8 moles) of 80% propargyl bromide/toluene in 800 ml THF at −78° C. The mixture was warmed slowly to room temperature over a 1 hour period, then it was poured into cold dilute hydrochloric acid and extracted with ether. The ether extracts were combined, dried, filtered and concentrated to give 216 g of a light brown oil which was used immediately in the next reaction without further purification.

1-Cyclohexyl-1-hydroxy-1-phenyl-7-dimethylaminohept-5-yn-2-one

To a stirred solution of 20 g (0.67 mole) of paraformaldehyde, 75 g (0.67 mole) of 40% dimethylamine in water and 200 mg of copper acetate in 50 ml of dioxane heated to 60° C. for 1 hour was added a solution of 216 g (0.63 mole) of the acetylenic ketone in 150 ml of dioxane. The mixture was stirred at 90° C. for 3 hours, then it was cooled to room temperature and 200 ml of cold 10% aqueous KOH was added. The resulting slurry was filtered through celite and the celite pad washed with 1 L of ether. The ether layer was extracted with cold dilute hydrochloric acid. The aqueous acid layer was then neutralized with sodium bicarbonate and extracted with ether. The ether extracts were combined, dried and concentrated to give a brown oil which was purified by chromatography (florisil, 30% EtOAc/hexane then 10% methanol/methylene chloride) to give 170 g (82% from the siloxy ketone) as a light brown oil. Treatment of this oil with an excess of fumaric acid in methanol-ether gave colorless crystals of a hemifumarate hemihydrate, mp 113°–115° C.

EXAMPLE VII

(R)-1-Cyclohexyl-1-hydroxy-1-phenyl-2-propanone

To a mixture of 315 ml of 1.4M CH$_3$Li (0.44 mole) in ether and 750 ml of THF at room temperature was added a solution of 26 g (0.11 mole) of (R)-cyclohexylmandelic acid, prepared by the method of R. B. Barlow, F. M. Franks, and J. D. M. Pearson, J. Med. Chem., 16, 439 (1973), in THF. Following the addition, the mixture was stirred at room temperature for 3.5 hours and then brought to reflux for 3 hours. The mixture was cooled and then added dropwise to a mixture of 300 ml of glacial acetic acid and 700 ml of water. This mixture was extracted with ether, the organic layer was separated, washed with water and saturated aqueous sodium bicarbonate, dried, and the solvent removed. The mixture was distilled to give 20 g of clear oil (bp 120° C., 0.1 mm Hg), NMR (chloroform-d) δ7.5(m, 5H), 4.5(S, 1H), 2.4(t, 1H), 2.0(s, 3H), 1.9–1.0(m, 10H).

(R)-1-Cyclohexyl-1-phenyl-1-trimethylsiloxy-2-propanone

To a solution of 12 ml (95 mmoles) of trimethylsilyl chloride and 11.6 g (172 mmoles) of imidazole in 100 ml of DMF was added 20 g (86 mmoles) of (R)-1-cyclohexyl-1-hydroxy-1-phenyl-2-propanone. This mixture was heated to 85° C. overnight. The next day, the mixture was cooled and poured onto a mixture of 100 ml of petroleum ether and 100 ml of ether. This was extracted with water. The organic layer was separated, dried, and the solvent removed. The residue was chromatographed on silica gel with hexane as the eluent to give 18.0 g of clear oil. IR 2950, 1730 cm$^{-1}$ NMR (CDCl$_3$) δ7.4(m, 5H), 2.3(t, 1H), 2.1(s, 3H), 1.9–1.0(m, 10H), 0.3(s, 9H).

(R)-1-Cyclohexyl-1-hydroxy-1-phenyl-7-(dimethylamino)hept-5-yn-2-one Hemifumarate Hydrate To a solution of 6.6 ml (0.031 mole) of hexamethyldisilizane in 350 ml of THF at 0° C. was added 14.35 ml (0.031 mole) of a 2.2M solution of n-BuLi in hexane. The mixture was stirred for 30 minutes, and then a solution of 8 g (0.026 mole) of (R)-1-cyclohexyl-1-phenyl-1-trimethylsiloxy-2-propanone in 50 ml of THF was added dropwise. The reaction mixture was stirred for 45 minutes and then it was added dropwise to a solution of 11 ml (0.1 mole) of propargyl bromide in 350 ml of THF at −78° C. Following the addition, the cooling bath was removed and the mixture allowed to warm to room temperature over a 3 hour period. It was then partitioned between ether and water. The organic layer was washed three times with water and once with brine, dried and concentrated. The crude mixture was carried on to the next step.

To a solution of 8 grams of 40% aqueous dimethylamine in 30 ml of dioxane was added 1 g of paraformaldehyde. This mixture was heated at 60° C. for 30 minutes and then the crude reaction mixture from above was added as a solution in 100 ml of dioxane. This was heated at 90° C. for one hour and allowed to cool. It was partitioned between ether and saturated sodium bicarbonate. The organic layer was separated, washed three times with water, once with brine, dried, and the solvent removed under reduced pressure. The residue was chromatographed on silica gel and eluted with a gradient from hexane to 3% triethylamine: 20% ethyl acetate: 77% hexane to give 6.0 g of a heavy oil, homogeneous by GLPC.

This compound was dissolved in 250 ml of THF and cooled to 0° C. To this solution was added 7.8 g (25 mmoles) of tetrabutylammonium fluoride. The mixture was stirred for one hour and then partitioned between ether and saturated sodium bicarbonate. The organic layer was separated, washed three times with water, once with brine, dried, and the solvent removed under reduced pressure. The residue was chromatographed on silica gel and eluted with a gradient from 1% methanol in methylene chloride to 10% methanol in methylene chloride to give 3.1 g of a heavy oil, homogeneous by GLPC. The material was dissolved in ether and to the solution was added 0.58 g of fumaric acid in 6 ml of methanol. The mixture was stirred for 10 minutes and the solvent was removed under reduced pressure. The residue was suspended in 250 ml of ether and cooled to 0° C. The solid was isolated by filtration and dried under high vacuum. Mp 108°–110° C.; NMR (CDCl$_3$) δ7.5(m, 5H), 6.8(s, 1H), 3.4(s, 2H), 2.8(m, 2H), 2.5(m, 2H), 2.4(m, 3H), 1.8(m, 3H), 1.5(m, 1H), 1.2(m, 7H); IR 3400, 2980, 1710 cm$^{-1}$; TLC (silica gel, 3% triethylamine: 20% ethyl acetate: 77% hexane) Rf=0.24; (c=1, MeOH)= +27.19°; Anal. Calcd. for C$_{21}$H$_{29}$NO$_2$.0.5C$_4$H$_4$O$_4$.0.5H$_2$O: C 70.02; H 8.17; N 3.55. Found: C 70.07, 70.00; H 8.06, 8.07; N 3.46.

The S enantiomer was prepared from (S)-cyclohexylmandelic acid (Barlow et al., loc. cit.) in the same fashion described for the R isomer, $[\alpha]^D_{20}$ (c=1, MeOH)−28.4°.

EXAMPLE VIII

3-Cyclohexyl-3-hydroxy-3-phenylpropyne

Lithium acetylide (47.84 g, 0.52 mole) was added to 70 ml of THF. The solution was cooled to 0° C. and a solution of cyclohexyl phenyl ketone in 100 ml of THF was added over a period of 15 minutes with stirring. The solution was allowed to warm to room temperature and stirred for 16 hours. The solution was then cooled to 0° C. and 50 ml of a 5N HCl was added. The solution was then warmed to room temperature and 200 ml of water was added. The solution was transferred to a separatory funnel and washed with ether. The ether washes were combined and dried. Upon removal of the ether under vacuum and vacuum distillation of the crude product a pale yellow oil was isolated (60.33 g, 82.9%): bp 111°–4° C. (0.8 mm), NMR (CDCl$_3$) δ7.7–7.2(m, 5H), 2.6(s, 1H), 2.3(s, 1H), 2.1–0.9(m, 11H). IR (neat) 3433, 3304, 2111, 1448, 1016 cm$^{-1}$.

1-Acetoxy-1-cyclohexyl-1-phenylpropan-2-one

3-Cyclohexyl-3-hydroxy-3-phenylpropyne (21.57 g, 0.10 mole) was added to 100 ml of glacial acetic acid. While the solution was stirred vigorously, mercuric acetate (35.20 g, 0.11 mole) was added. The solution was stirred at room temperature for 72 hours and then thioacetamide (8.3 g, 0.11 mol) was added. The solution was stirred an additional 3 hours and 300 ml of ether was added. The reaction mixture was transferred to a separatory funnel and washed with water, saturated aqueous sodium bicarbonate, and again with water. The ether layer was dried over sodium sulfate and the ether removed under vacuum to afford the product as a white crystalline solid (18.36 g, 66.9%), mp 81°–3° C. (from petroleum ether). NMR (CDCl$_3$) δ7.3(bs, 5H), 2.2(s, 3H), 1.9(s, 3H), 2.0–0.8(m, 11H).

1-Cyclohexyl-1-hydroxy-1-phenylpropan-2-one

To a solution of 1-acetoxy-1-cyclohexyl-1-phenylpropan-2-one (16.42 g, 0.06 mole) in 55 ml of a 90% aqueous methanol solution was added 3.2 g of potassium hydroxide. The solution was refluxed for 15 minutes, cooled, and 90 ml of a saturated aqueous sodium chloride solution was added. The reaction mixture was washed twice with ether. The ether washes were combined, dried and evaporated to dryness under vacuum.

The crude product was vacuum distilled to afford a clear oil (10.51 g, 75.4%), bp 125°–8° C. (0.1 mm). NMR (CDCl$_3$) δ7.6–7.2(m, 5H), 4.5(s, 1H), 2.1(s, 3H), 2.5–0.9(m, 11H). IR (neat) 3456, 3057, 1705, 1448, 1358, 1209, 1124 cm$^{-1}$.

1-Cyclohexyl-1-phenyl-1-trimethylsilyloxypropan-2-one

1-Cyclohexyl-1-hydroxy-1-phenylpropan-2-one (15.44 g, 66.5 mmole) was added to 35 ml of DMF. To this solution was then added bis(trimethylsilyl)acetamide (16.2 g, 79.7 mmole) and the reaction mixture was stirred at 130° C. under argon for 12 hours. The mixture was cooled and ether (100 ml) was added. The solution was washed twice with water, dried and evaporated to dryness under vacuum. Distillation by a Kugelruhr apparatus at 100° C. afforded a yellow oil (19.86 g, 98.1%). NMR (CDCl$_3$) δ7.6–7.2(m, 5H), 2.1(s, 3H), 2.4–0.9(m, 11H), 0.2(s, 9H). IR (neat) 1718, 1250, cm$^{-1}$.

1-Cyclohexyl-1-hydroxy-1-phenyl-7-bromohept-5-yn-2-one

To a dry flask under argon was added 1,1,1,3,3,3-hexamethyldisilazane (11.6 g, 71.6 mmole) and 75 ml of THF. The solution was cooled to −10° C. and n-BuLi (19.8 g, 71.3 mmol) was added directly to the reaction mixture. The solution was stirred at −10° C. for 30 minutes. A solution of 1-cyclohexyl-1-phenyl-1-trimethylsilyloxypropan-2-one (21.99 g, 72.2 mmol) in dry THF (75 ml) was added dropwise over a period of 15 minutes and the reaction mixture was stirred at −10° C. After the solution had stirred for 1 hour 1,4-dibromo-2-butyne (59.9 g, 0.3 mole) was added directly to the reaction mixture and the mixture was stirred an additional hour. The reaction was stopped by the dropwise addition of a solution of glacial acetic acid (7 ml) in ether (20 ml). The solution was warmed to room temperature and ether (150 ml) was added. The solution was washed with water followed by a saturated aqueous sodium chloride solution. The ether layer was dried and concentrated to afford a brownish liquid. This oil was dissolved in 150 ml of methanol and 0.2 ml of concentrated hydrochloric acid was added. The solution was stirred at 40° C. for 30 minutes and cooled to room temperature. Water was then added until the solution became cloudy and then 150 ml of ether was added. The solution was washed with a saturated aqueous sodium chloride solution, dried over sodium sulfate, and evaporated under vacuum to afford a yellowish brown oil. Purification on a silica column with a hexane:ethyl acetate solution (98:2 followed by 9:1) afforded an orange oil (16.1 g, 59.5%). NMR (CDCl$_3$) δ7.6–7.2(m, 5H), 4.3(s, 1H), 3.8(t, 2H), 2.8–2.6 (m, 2H), 2.5–2.3(m, 2H), 1.9–1.1(m, 11H). IR (neat) 3461, 2234, 1705, 609 cm$^{-1}$. TLC (silica, petroleum ether:ethyl acetate (95:5)) Rf=0.53.

1-Cyclohexyl-1-hydroxy-1-phenyl-7-diethylaminohept-5-yn-2-one

1-Cyclohexyl-1-hydroxy-1-phenyl-7-bromohept-5-yn-2-one (7.51 g, 17.2 mmol) was added to 75 ml of ether and diethylamine (70.7 g, 0.1 mol) was added. The flask was stoppered and stirred at room temperature for 3 hours. The solution was then filtered and washed twice with water, dried and concentrated to afford an orange oil. This oil was dissolved in carbon tetrachloride and evaporated to dryness three times to remove any traces of diethylamine to afford a yellowish orange oil (7.11 g, 100%). NMR (CDCl$_3$) δ7.6-7.2(m, 5H), 4.4(s, 1H), 3.3(t, 2H), 2.8-2.6(m, 2H), 2.3(q, 4H), 2.5-2.2(m, 2H), 1.9-1.0(m, 11H), 1.0(t, 6H). IR (neat) 3456, 1707 cm$^{-1}$. Hemifumarate salt: Mp, 140°-2° C. (from 2-butanone). NMR (CDCl$_3$) δ7.6-7.2(m, 5H), 6.8(s, 1H), 3.6(t, 2H, J=1.8), 2.9-2.7(m, 2H), 2.8(q, 4H, J=7.3), 2.5-2.3(m, 2H), 1.9-1.0(m, 11H), 1.1(t, 6H, J=7.2). IR (KBr) 2234, 1710 cm$^{-1}$. Anal. Calcd. for C$_{25}$H$_{35}$NO$_4$: C, 72.59; H, 8.55; N, 3.39. Found: C, 72.26, 72.17; H, 8.56, 8.59; N, 3.18.

Utilizing the appropriate substituted phenyl ketone and amine this general procedure was employed for the preparation of all of the remaining 1,7-substituted-1-hydroxyhept-5-yn-2-ones described in Examples IX and X, whose preparation was not detailed in Examples I–VII. 1-Cyclohexyl-1-fluoro-1-phenyl-7-diethylaminohept-5-yn-2-one was similarly prepared utilizing 1-cyclohexyl-1-fluoro-1-phenyl-2-propanone derived by fluorination of the corresponding hydroxylated compound. 1-Cyclohexyl-1-phenyl-7-diethylamino-5-yn-2-one was also prepared in a similar manner using 1-cyclohexyl-1-phenyl-2-propanone.

EXAMPLE IX

In Examples IX and X the test compounds are as follows:

| Compound No. | Compound Name |
| --- | --- |
| 1. | 1,1-Diphenyl-1-hydroxy-7-diethylaminohept-5-yn-2-one |
| 2. | 1-Cyclohexyl-1-phenyl-1-hydroxy-7-diethylaminohept-5-yn-2-one |
| 3. | 1-Cyclopentyl-1-phenyl-1-hydroxy-7-diethylaminohept-5-yn-2-one |
| 4. | 2-Hydroxy-2-phenyl-8-(N,N-diethylamino)oct-6-yn-3-one |
| 5. | 1-Cyclohexyl-1-hydroxy-1-phenyl-7-diisopropylaminohept-5-yn-2-one |
| 6. | 1-Cyclohexyl-1-hydroxy-1-phenyl-7-ethylaminohept-5-yn-2-one |
| 7. | 1-(6-Diethylaminohex-4-yn-2-one)-1-hydroxy-1,2,3,4-tetrahydronaphthalene |
| 8. | 1-Cyclohexyl-1-hydroxy-1-phenyl-7-(N-methyl-N-ethylamino)hept-5-yn-2-one |
| 9. | 1-Cyclohexyl-1-hydroxy-1-phenyl-7-isopropylaminohept-5-yn-2-one |
| 10. | 1-Cyclohexyl-1-hydroxy-1-phenyl-7-(N-methyl-N-isopropylamino)hept-5-yn-2-one |
| 11. | 1-Cyclohexyl-1-phenyl-7-diethylaminohept-5-yn-2-one |
| 12. | 1-Cyclohexyl-1-hydroxy-1-phenyl-7-t-butylaminohept-5-yn-2-one |
| 13. | 1-Cyclohexyl-1-hydroxy-1-phenyl-7-(N-ethyl-N-isopropylamino)hept-5-yn-2-one |
| 14. | 1-Cyclohexyl-1-hydroxy-1-phenyl-7-dimethylaminohept-5-yn-2-one |
| 15. | 1-Cyclohexyl-1-hydroxy-1-phenyl-7-(N-methyl-N-phenethylamino)-hept-5-yn-2-one |
| 16. | 1-Cyclohexyl-1-hydroxy-1-phenyl-7-pyrrolidinylhept-5-yn-2-one |
| 17. | 1-(6-N,N-Diethylaminohex-4-yn-2-one)-1-hydroxyindan oxalate |
| 18. | 1-Cyclohexyl-1-hydroxy-1-phenyl-7-methylaminohept-5-yn-2-one |
| 19. | 1-Cyclohexyl-1-fluoro-1-phenyl-7-dimethylaminohept-5-yn-2-one |
| 20. | 1-Cyclohexyl-1-hydroxy-1-phenyl-7-(N,N-diethyl-N-methylammonio)-hept-5-yn-2-one iodide |
| 21. | 1-Cyclohexyl-1-hydroxy-1-phenyl-7-(N-methyl-N-benzylamino)-hept-5-yn-2-one |
| 22. | 1-Cyclopentyl-1-hydroxy-1-phenyl-7-(N-methyl-N-ethylamino)-hept-5-yn-2-one |
| 23. | 1-Cyclopropyl-1-hydroxyl-1-phenyl-1-diethylamino-hept-5-yn-2-one |
| 24. | 1-Cyclohexyl-1-hydroxy-1-phenyl-7-aminohept-5-yn-2-one |
| 25. | 1-Cyclohexyl-1-hydroxy-1-phenyl-7-dibutylaminohept-5-yn-2-one |
| 26. | 1-Cyclopentyl-1-hydroxy-1-phenyl-7-dimethylaminohept-5-yn-2-one |
| 27. | 5-(6-N,N-Diethylamino-1-oxohex-4-ynyl)-5-hydroxy-6,7,8,9-tetrahydrobenzocycloheptene |
| 28. | 1-Cyclopropyl-1-hydroxy-1-phenyl-7-(N-methyl-N-ethylamino)-hept-5-yn-2-one |
| 29. | 1-Cyclohexyl-1-hydroxy-1-phenyl-7-dipropylamino)-hept-5-yn-2-one |
| 30. | 1,1-Diphenyl-1-hydroxy-7-ethylaminohept-5-yn-2-one |
| 31. | 1,1-Diphenyl-1-hydroxy-7-(N-ethyl-N-methylamino)-hept-5-yn-2-one |
| 32. | 1,1-Diphenyl-1-hydroxy-7-dimethylaminohept-5-yn-2-one |
| 33. | 1-Cyclopropyl-1-hydroxy-1-phenyl-1-ethylaminohept-5-yn-2-one |
| 34. | 1-Cyclopropyl-1-hydroxy-1-phenyl-7-dimethylamino-hept-5-yn-2-one |
| 35. | 1-Cyclohexyl-1-hydroxy-3-methyl-1-phenyl-7-dimethylamino-hept-5-yn-2-one |
| 36. | 1-(1-Adamantyl)-1-hydroxy-1-phenyl-7-dimethylaminohept-5-yn-2-one |
| 37. | 1-Cyclohexyl-1-hydroxy-1-(4-fluorophenyl)-7-dimethylaminohept-5-yn-2-one |
| 38. | 1-Cyclohexyl-1-hydroxy-1-(4-fluorophenyl)-7-ethylaminohept-5-yn-2-one |
| 39. | (S)-1-Cyclohexyl-1-hydroxy-1-phenyl-7-dimethylamino-hept-5-yn-2-one |
| 40. | 1-Cyclohexyl-1-hydroxy-1-phenyl-7-[N-(2-hydroxyethyl) N-methylamino]hept-5-yn-2-one |
| 41. | 1-Bicyclo [2.2.1]hept-2-yl-1-hydroxy-1-phenyl-7-dimethylaminohept-5-yn-2-one |
| 42. | 1-Bicyclo [2.2.1]hept-2-yl-1-hydroxy-1-phenyl-7-ethylaminohept-5-yn-2-one |
| 43. | (R)-1-Cyclohexyl-1-hydroxy-1-phenyl-7-dimethylamino-hept-5-yn-2-one |
| 44. | 1-Cyclobutyl-1-hydroxy-1-phenyl-7-dimethylaminohept-5-yn-2-one |
| 45. | 1-Cyclobutyl-1-hydroxy-1-phenyl-7-ethylamino-hept-5-yn-2-one |
| 46. | 1-Cyclobutyl-1-hydroxy-1-phenyl-7-(N-ethyl-N-methylamino)-hept-5-yn-2-one |
| 47. | 3-Hydroxy-2-methyl-3-phenyl-9-dimethylamino-non-7-yn-4-one |
| 48. | 1-(1-Methylcyclopropyl)-1-hydroxy-1-phenyl-7-dimethylaminohept-5-yn-2-one |
| 49. | 4-Hydroxy-2-methyl-4-phenyl-10-dimethylamino-dec-8-yn-5-one |

ANTIMUSCARINIC PROTOCOL

Purpose

This protocol is designed to identify compounds that possess antagonist activity at postsynaptic muscarinic cholinergic receptors on intestinal (ileal) longitudinal smooth muscle and bladder detrusor muscle.

Materials and Methods

Preparation of Ileum for Testing

Male albino guinea-pigs are killed by decapitation or cervical dislocation. The cavity is opened and the small intestine is removed, with about 10 cm of the terminal ileum being discarded. The intestine is placed in a Petri dish that contains Tyrodes solution (137 mM NaCl, 2.7 mM KCl, 1.8 mM CaCl$_2$.2H$_2$O, 1.1 mM MgCl$_2$.6H$_2$O, 0.4 mM NaH$_3$PO$_4$, 11.8 mM NaHCO$_3$, 5.6 mM dextrose) and cut into 3-4 cm segments. The segments are preferentially taken from the aboral end of the ileum. Each segment is carefully stretched onto a glass rod 6 mm in diameter and the remaining mesenteric tissue is cut away. The longitudinal muscle, with the myenteric plexus attached, is separated from the underlying circular muscle by gently stroking with a cotton-tipped applicator soaked in Tyrodes solution on a tangent away from shallow longitudinal incisions made parallel to the mesenteric attachment. Using gentle traction, and taking care to keep the segment moist throughout the whole procedure, the tissue is stripped from the whole length of the segment (Paton and Zar, J. Physiol. 194:13, 1968).

Tissues are suspended with 5-0 silk suture in 10 ml water-jacketed glass tissue baths containing Tyrodes solution maintained at 37° C. and bubbled with 95% $O_2$/5% $CO_2$. The suture connects each tissue to a isometric force-displacement transducer (Grass or Gould) coupled to a physiograph. Each preparation is suspended under a resting tension of 0.3 g and allowed to equilibrate for 36 minutes. During this period, the baths are emptied and filled every 12 minutes with 10 ml warm Tyrodes solution. At the end of this equilibration period, each muscle strip is conditioned by adding 10 μm carbachol to the baths. The drug remains in contact with each tissue for 1-2 minutes and then is removed from the bath with 4 rapid rinses of 10 ml warm Tyrodes solution. The preparations are allowed to recover for an additional 12 minutes before being used in experiments.

Preparation of Bladder for Testing

Male albino guinea-pigs are killed by decapitation or cervical dislocation. The peritoneal cavity is opened and the bladder is held lightly at its apex, stretched gently, and fat is lifted with fine forceps and dissected away in situ with blunt-tipped scissors as close to the surface of the bladder as possible. The tissue is placed in a latex-bottomed Petri dish that contains a modified Krebs solution (133 mM NaCl, 1.3 mM $NaH_3PO_4$, 16.3 mM $NaHCO_3$, 4.7 mM KCl, 0.6 mM $MgSO_4.7H_2O$, 2.5 mM $CaCl_2.2H_2O$, 7.7 mM dextrose) and cut above the neck. The bladder is collapsed into a flat pouch, which is opened by two lateral incisions and unfolded to give a rectangular sheet of tissue approximately 2 cm long and 1 cm wide. The sheet is gently stretched and pinned to the bottom of the Petri dish. Blunt separation of the mucosa, which is visible as a looser superficial pink layer, is started at one end by carefully inserting the blades of micro dissecting scissors between the mucosa and muscle layers and using gentle spreading of the blades, together with steady traction with forceps to tease the two layers apart. Clean removal of the mucosa is usually possible without any fraying or tearing of the underlying muscle. The removal of the mucosa is considered essential for improving oxygen supply to the preparation and for providing better access on both sides of the thin muscle sheet for administered drugs (Ambache and Zar, J. Physiol. 210:671, 1970). The sheet is trimmed, if necessary, and cut longitudinally into four strips.

The strips are tied off with 5-0 silk suture and are then suspended in 10 ml water-jacketed glass tissue baths containing the Krebs solution maintained at 35° C. and bubbled with 95% $O_2$/5% $CO_2$. The suture connects each tissue to a isometric force-displacement transducer (Grass or Gould) coupled to a physiograph. Each preparation is suspended under a resting tension of 0.5 g and allowed to equilibrate for 36 minutes. During this period, the baths are emptied and filled every 12 minutes with 10 ml warm Krebs buffer. At the end of this period, each muscle strip is conditioned by adding 10 μM carbachol to the baths. The drug remains in contact with each tissue for 1-2 minutes and then is removed by four rapid rinses of 10 ml warm Krebs buffer. The preparations are allowed to recover for an additional 12 minutes before being used in experiments.

Preparation of Agonist

Carbachol is dissolved in saline to produce $2\times10^{-2}$M stock concentrations. Serial dilutions (1:10) in saline or water are made from the stock solution. Appropriate volumes of these solutions are added cumulatively to the 10 ml tissue baths in order to obtain the desired bath concentrations.

Preparation of Test Compounds

Compounds that are soluble in water or saline are dissolved in these solvents to produce $2\times10^{-2}$ or $2\times10^{-3}$M stock concentrations. Small amounts of 1N NCl or NaOH, or 95% ethanol may be added for those agents that are not soluble in water or saline alone. Serial dilutions (1:10) in saline or water are made from the stock solution. Compounds that are insoluble in aqueous solvents are dissolved in dimethylsulfoxide (DMSO) to produce $4\times10^{-2}$M stock solutions. Serial dilutions (1:10) in water are made from the stock solution. Other solvents may be used when appropriate and will be specifically described in the experimental procedure. Appropriate volumes are then added to the baths in order to obtain the desired bath concentrations.

Experimental

Appropriate volumes of carbachol solutions are cumulatively added to the 10 ml tissue baths to increase the concentration of carbachol in the bath step-by-step without washing out after each single dose. With each concentration step, the tissue contracts isometrically. The next concentration is added only after the preceding contraction has reached a steady value. When the next concentration step does not cause a further increase in contraction, it is assumed that the maximum effect has been obtained. The tissue is then washed with 4 rapid rinses of 10 ml warm Tyrodes solution and allowed to recover for 12 minutes (Van Rossum et al., Arch. int. Pharmacodyn. 143:240, 1963 and 143:299, 1963). Antagonism of carbachol responses in the presence of antagonist are determined by repeating the cumulative addition procedure after the tissue has been exposed to the agonist for 5 minutes.

Three or four different concentrations of antagonist are studied in the same preparations. Responses are expressed relative to the maximum contraction elicited by carbachol in the absence of antagonist. The data are collected via Buxco Data Logger and analyzed by Branch Technology's software package to obtain Kb values for the antagonists.

TABLE I

Antimuscarinic Activity in Guinea Pig Bladder and Ileum

| Compound | Bladder Kb (nM) | Ileum Kb (nM) |
|---|---|---|
| Atropine | 4.8 | 2.5 |
| (R,S)-Oxybutynin | 41.6 | 23 |
| (S)-Oxybutynin | 269 | 103 |
| (R)-Oxybutynin | 21 | 2.0 |
| 1 | 70.7 | |
| 2 | 175 | 134 |
| 3 | 38.3 | 42 |
| 4 | 5200 | |
| 5 | 260 | 600 |
| 6 | 232 | 90 |

TABLE I-continued
Antimuscarinic Activity in Guinea Pig Bladder and Ileum

| Compound | Bladder Kb (nM) | Ileum Kb (nM) |
| --- | --- | --- |
| 7 | 3070 | >10000 |
| 8 | 37 | 17 |
| 9 | 292 | 142 |
| 10 | 267 | 432 |
| 11 | 756 | |
| 12 | 4300 | |
| 13 | 217 | |
| 14 | 39 | |
| 15 | 551 | |
| 16 | 202 | 90 |

TABLE II
Antimuscarinic Activity in Guinea Pig Bladder

| Compound | Bladder Kb(nM) |
| --- | --- |
| 17 | >10000 |
| 18 | 71 |
| 19 | >10000 |
| 20 | 596 |
| 21 | 4200 |
| 22 | >10000 |
| 23 | 58 |
| 24 | 2100 |
| 25 | >10000 |
| 26 | >10000 |
| 27 | 1290 |
| 28 | 241 |
| 29 | 142 |
| 30 | 200 |
| 31 | 75 |
| 32 | 70 |
| 33 | 224 |
| 34 | 35 |
| 35 | 163 |
| 36 | >10000 |
| 37 | 68 |
| 38 | 504 |
| 39 | 209 |
| 40 | 257 |
| 41 | 90 |
| 42 | 65 |
| 43 | 17 |
| 44 | 4.9 |
| 45 | 23 |
| 46 | 7.5 |
| 47 | 43 |
| 48 | 24 |
| 49 | 30.5 |

EXAMPLE X
Duration of Action Studies with in Vivo Guinea Pig Cystometrogram Model Introduction To assess test compounds with a more intact model system, a method which more closely mimics the natural slow filling of the bladder is used. The slow-filling cystometrogram (CMG) is used clinically to evaluate urinary bladder dysfunction (Ouslander, J., et al., J. Urol., 137:68-71 (1987)).

This clinical CMG is produced by catheterizing the bladder so it may be filled, emptied and refilled with fluid while simultaneously measuring the internal bladder pressure (Pves). Since the rate of filling can alter the response of the reflex system (Coolsaet, B. Neurourol. Urodyn., 4:263-273 (1985)), a slow rate is chosen. This allows the bladder to reach maximum capacity/pressure before sensory systems initiate the normal urge and micturition reflex patterns. We use a modification of this clinical test to determine duration of action of test compounds by repeated filling of the bladder following i.v. administration of the test compound. Peak pressure above the threshold pressure is the primary measure of action which can be inhibited by the test compounds and can be used to determine potency and duration of action in this anesthetized guinea pig model.

Methods

Animal Subjects

Female guinea pigs (350-500 g, outbred stock from Charles River Laboratories, origin: Crl: (HA)BR Hartley, raised and kept as V.A.F.) fed Ralston Purina Guinea Pig Chow #5025 and tap water ad libidem and kept in small groups (<5) at 70°±2° F., RH 40-50%, 12 hour light/dark cycle.

Anesthesia

Urethane (available from Sigma, #U-2500, 1.5 gm/kg i.p.) injection made as 150 mg/ml urethane in water, is given in divided doses of 80% +20% about 30 min apart due to potential for overdose if delivered in single dose. This maintains a stable level of anesthesia for 3 or more hours without supplements.

Animal Preparation

After induction of anesthesia, the animals are shaved about the medial thigh area for later femoral vein exposure and injection. They are placed supine on a heated small animal board to maintain body temperature. A saline-filled urinary catheter made of PE-100 tubing with several lateral holes near the distal tip is placed into the bladder through the urethra. Care is taken to not allow any air into the system and the tip of the catheter is lubricated with a drop of mineral oil. The catheter is connected by a series of 3-way stopcocks to a pressure transducer (Statham/Gould Model P-50), a syringe pump (Harvard Model 2274) and an exit port to empty the bladder after filling. The bladder is emptied by gentle syringe suction at the opened exit port combined with gentle manipulation and pressure on the lower abdomen. It is then rinsed out with 2-3 ml of saline and emptied again. The urethral opening is sealed about the catheter with a purse-string suture (4-0 Dermalon or silk, using a ⅜-circle cutting needle, e.g. P-3). The syringe pump is set to deliver normal saline at room temperature at approximately 0.4 ml/minute with the exit port closed and the transducer open to measure the intravesicular bladder pressure during the filling process. The transducer is balanced and calibrated prior to each experiment using a column of water. For most animals, a full-scale range of 0 to 5.0 kPa (equivalent to 0 to 51 cm $H_2O$) is most useful. In some cases, peak contraction pressure will exceed 5 kPa and a rapid switch to a 0 to 10 kPa scale is needed to detect the peak response. A chart recorder (Gould=Model 2400S) records Pves at a chart speed of 0.10 mm/sec.

Drug Preparation

Test drugs and reference compounds are normally prepared as a solution in normal saline, acidified or made basic as needed to get the compound into solution at the desired concentration. Drugs are delivered at selected mg/kg (calculated as free base) doses i.v. in a volume of approximately 0.5 to 0.8 ml. The selection of the desired dose to test for duration of action is based on preliminary studies where dose-response data are obtained using an escalating dose series of measures on the paradigm below. Normally for an inhibition measure, the $ID_{70}$-$ID_{80}$ is selected so that sufficient signal depression is observed but that the signal is not obliterated or masked by the noise of the test system.

Measurement Paradigm

After "resting" the bladder empty for 5-10 min, the saline infusion is started. The Pves is measured as the filling occurs. For most animals, a point will be reached within 3 to 15 minutes (approximate bladder volume of 1.2 to 6 ml) where a strong contraction occurs during this first control filling maneuver. When this is recognized and the peak pressure has subsided, the bladder is emptied as noted above and a 5 minute rest period begins. The control fills are repeated with the fixed rest periods at least three times to establish a reproducible baseline control set. A useful average of the last three fills before the drug treatment is the objective of the repeated control fill maneuvers.

In some animals, a recognizable contraction response is not evident and/or the bladder appears to be not compliant (the pressure rises continuously and rapidly as volume increases). If the contraction response does not appear within 20 minutes (about 8 ml volume) or the continuously rising Pves exceeds 2.5-3 kPa, empty the bladder and begin the fixed 5 minute rest period. Nearly all animals will begin to produce typical control responses after two or three filling maneuvers.

The following measurements are taken from the chart record:

PvesB = the baseline pressure at the beginning of a fill maneuver

PvesT = the threshold pressure where the observed contraction response begins

PvesM = the absolute maximum Pves during the contraction response

PvesP = PvesM−PvesT: peak pressure above threshold pressure

Time = Infusion period until PvesT is noted (Volume of the bladder is then the actual delivery rate × time, ignoring any kidney output)

After the last of the desired control fills, the femoral vein is exposed and the test drug is delivered i.v. during the midpoint of the fixed 5 minute rest period. The filling maneuvers are then repeated to observe the changes of the recorded parameters over time following the test drug administration. Peak pressure above the threshold (PvesP) is used as the primary measure of inhibition of contraction strength for the duration of action of the test compounds.

Analysis

Measurements of the listed parameters are tabulated and values for control measures averaged (usually the last three control fills) and used to compare with the post-treatment results. PvesP (and any other parameter) is then transformed to percent change from control:

((Result/Control average)*100)−100 and plotted against time since drug administration.

Because each animal serves as its own control and there is normal variability between animals, this parameter is then normalized to 100% of maximum response (i.e. maximum depression) so that the maximum depression of control is now defined as 100% of the observed depression. All measures over time then relate to the maximum depression observed.

Using the normalized response, plots are obtained of this measure against time since drug administration. For each animal, the plot is examined and a linear regression line is plotted to determine the slope of recovery of the normalized parameter (slope is thus in terms of %/min). Extreme tail points of data are deleted when appropriate using significance of slope criteria. This selects ponts where the slope begins to significantly differ from zero and includes the previous point at either end of the response recovery curve as appropriate. The regression line is then recalculated. Half-life of the parameter recovery is then taken without regard to the original intercept as:

$T\frac{1}{2} = 50/\text{slope. (min)}$

Because half-life measures are known to not be normally distributed, the geometric mean (G.M.) and the range of values are reported for each drug treatment or dose for comparison to other treatments. Ordinary tests of significance between drug treatments can then be made on either the regression parameters of the recovery curves or by using Student's t test on the values calculated for $T\frac{1}{2}$. The $ID_{50}$ is the calculated dose of compound which produces 50% of the maximal inhibition PvesP contraction strength parameter.

Results 1,7-Substituted heptyn-2-ones were tested in this model to determine $T\frac{1}{2}$ values for recovery toward control levels of the PvesP contraction strength parameter (Table III). The doses selected to test for duration of action were based on the estimates of the $ID_{70}$-$ID_{80}$ from prior studies and relate to equipotent doses for this measured parameter.

Many of the drugs showed either the same or shorter half-lives of PvesP depression than oxybutynin. Also, many exhibited significantly longer values.

TABLE III

CONTRACTION INHIBITION HALF-LIFE WITH in vivo GUINEA PIG CYSTOMETROGRAM (CMG) AT EQUIEFFECTIVE* INHIBITORY DOSES AND INHIBITORY EFFECTIVENESS ($ID_{50}$) FOLLOWING BOLUS i.v. INJECTIONS

| COMPOUND | DOSE (mg/kg) | $T\frac{1}{2}$ (G.M., range) (min.) | n§ | $ID_{50}$ (mg/kg) |
|---|---|---|---|---|
| Atropine | 0.03 | 60.5 (40–81) | 4 | 0.01 |
| Oxybutynin | 1.0 | 43.2 (31–69) | 7 | 0.14 |
| 2 | 3.0 | 29.4 (18–38) | 10 | 2.8 |
| 3 | 4.0 | 26.3 (18–42) | | |
| 5 | 10.0 | 31.8 (29–35) | 2 | 5.3 |
| 6 | 3.0 | 82.4 (46–120) | 10 | 0.98 |
| 7 | 10.0* | 42.0 (32–56) | 2 | 4.6 |
| 8 | 2.0 | 38.0 (32–51) | 4 | 0.45 |
| 9 | 3.0 | 34.0 (27–46) | 6** | 2.1 |
| 10 | 10.0* | 38.8 (24–56) | 4 | 4.2 |
| 13 | 8.5 | 20.7 (12–35) | 3 | 3.3 |
| 14 | 3.0 | 122.6 (71–193) | 11 | 0.48 |
| 15 | — | — | — | >10 |
| 16 | 10.0 | 43.2 (38–51) | 4 | >10 |
| 18 | 1.0 | 47.0 (35–58) | 4 | 0.48 |
| 20 | 10.0 | 25.0 (8–33) | 3 | — |
| 21 | 10.0 | No effect at 10 | 2 | — |
| 22 | — | — | — | No effect |
| 23 | 6.0 | 78.0 (73–94) | 4 | 0.98 |
| 27 | 10.0 | 29.0 (14–42) | 4 | — |
| 28 | 7.0 | 125.0 (76–289) | 6 | 1.26 |
| 29 | 10.0 | 75.0 (47–136) | 4 | 2.63 |
| 30 | 14.0 | 54.0 (51–58) | 3 | 1.48 |
| 31 | 5.0 | 69.0 (45–83) | 3 | 0.90 |
| 32 | 4.0 | 44.0 (39–52) | 3 | 0.59 |
| 33 | 15.0 | 103.0 (67–140) | 3 | 1.1 |
| 34 | 3.0 | 88.0 (21–35) | 4 | 0.48 |
| 35 | 11.0 | 37.0 (26–51) | 3 | 2.1 |
| 37 | 9.0 | 102.0 (76–134) | 4 | 0.9 |
| 38 | 9.0 | 114.0 (113–120) | 3 | 1.8 |
| 39 | 18.0 | 85.0 (82–97) | 3 | 3.6 |

TABLE III-continued

CONTRACTION INHIBITION HALF-LIFE WITH
in vivo GUINEA PIG CYSTOMETROGRAM (CMG) AT
EQUIEFFECTIVE* INHIBITORY DOSES AND
INHIBITORY EFFECTIVENESS ($ID_{50}$)
FOLLOWING BOLUS i.v. INJECTIONS

| COMPOUND | DOSE (mg/kg) | $T_{\frac{1}{2}}$ (G.M., range) (min.) | n§ | $ID_{50}$ (mg/kg) |
|---|---|---|---|---|
| 41 | 9.0 | 240.0 (149–388) | 5 | 0.9 |
| 42 | 12.0 | 164.0 (103–272) | 4 | 1.13 |
| 43 | 2.0 | 310.0 (178–425) | 4 | 0.19 |
| 44 | 4.0 | 226.0 (148–334) | 3 | 0.12 |
| 45 | 9.0 | 144.0 (110–194) | 4 | 0.48 |
| 46 | 8.0 | 166.0 (130–212) | 3 | 0.86 |
| 47 | 3.5 | 79.8 (73–89) | 3 | 0.48 |
| 48 | 8.0 | 291.0 (174–483) | 3 | 0.28 |
| 49 | — | — | 4 | 4.08 |

*Number of animals
*Some drugs could not be delivered at a dose high enough for "equipotent" depression of this parameter; for these, the highest dose used is reported.
**Two animals with extreme high values ($T_{\frac{1}{2}}$ = 495 and 146 minutes) were excluded from this set. The G.M. with those values included is 57.0 min.
§n = number of animals.

What is claimed is:

1. A compound of the formula:

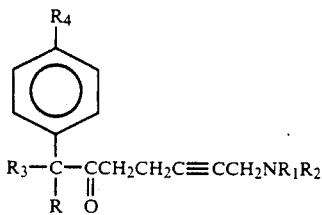

wherein
R is cycloalkyl having three to six carbon atoms, methylcyclopropyl, or polycycloalkyl having seven to eleven carbon atoms;
$R_1$ and $R_2$ are methyl;
$R_3$ is hydroxy; and
$R_4$ is hydrogen or fluorine;
and the pharmaceutically acceptable salts thereof.

2. The compound of claim 1 wherein R is cyclohexyl, cyclopentyl, cyclobutyl, cyclopropyl or admantane.

3. The compound of claim 1 wherein R is cyclobutyl.

4. The compound of claim 1 wherein $R_4$ is fluoro.

5. The compound of claim 1 which is 1-cyclobutyl-1-phenyl-1-hydroxy-7-dimethylaminohept-5-yn-2-one hydrochloride salt.

6. The compound of claim 1 which is 1-cyclohexyl-1-phenyl-1-hydroxy-7-dimethylaminohept-5-yn-2-one or the salt thereof.

7. The compound of claim 1 which is 1-cyclobutyl-1-phenyl-1-hydroxy-7-dimethylaminohept-5-yn-2-one or the salt thereof.

8. A method of treating neurogenic bladder disorder comprising administering to a patient suffering from said disorder a pharmaceutically effective amount of a compound having the formula:

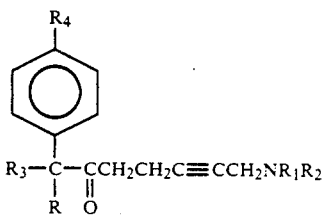

wherein
R is cycloalkyl having three to six carbon atoms, methylcyclopropyl or polycycloalkyl of seven to eleven carbon atoms;
$R_1$ and $R_2$ are methyl;
$R_3$ is hydroxy; and
$R_4$ is hydrogen or fluorine;
and the pharmaceutically acceptable salts thereof.

9. The method of claim 8 wherein the compound which is administered is 1-cyclohexyl-1-phenyl-1-hydroxy-7-dimethylaminohept-5-yn-2-one or the salt thereof.

10. The method of claim 8 wherein the compound which is administered is 1-cyclobutyl-1-phenyl-1-hydroxy-7-dimethylaminohept-5-yn-2-one or the salt thereof.

11. The method of claim 8 wherein the compound which is administered is 1-cyclobutyl-1-phenyl-1-hydroxy-7-dimethylaminohept-5-yn-2-one hydrochloride salt.

* * * * *